United States Patent [19]

Smith

[11] Patent Number: 5,195,959
[45] Date of Patent: Mar. 23, 1993

[54] ELECTROSURGICAL DEVICE WITH SUCTION AND IRRIGATION

[75] Inventor: Paul C. Smith, 2930 Blaisdell Ave. South Apt. #317, Minneapolis, Minn. 55408

[73] Assignee: Paul C. Smith, Minneapolis, Minn.

[21] Appl. No.: 708,208

[22] Filed: May 31, 1991

[51] Int. Cl.$^5$ .............................................. A61B 17/39
[52] U.S. Cl. ...................................... 604/34; 606/41; 606/42; 606/49; 604/35
[58] Field of Search ................. 604/22, 30, 34, 902, 604/35; 606/27, 29, 31, 39, 41, 42, 45, 49

[56] References Cited

U.S. PATENT DOCUMENTS

| | | | |
|---|---|---|---|
| 3,828,780 | 8/1974 | Morrison, Jr. | 604/902 |
| 4,427,006 | 1/1984 | Nottke | 606/42 |
| 4,567,838 | 1/1986 | Walker | 606/45 |
| 4,619,258 | 10/1986 | Pool | 606/42 |
| 4,696,669 | 9/1987 | Menhusen | 604/34 |
| 4,792,327 | 12/1988 | Swartz | 604/22 |
| 4,872,454 | 10/1989 | De Oliveira et al. | 606/42 |
| 4,941,872 | 7/1990 | Felix et al. | 604/902 |
| 5,035,695 | 7/1991 | Weber, Jr. et al. | 606/42 |
| 5,085,657 | 2/1992 | Ben-Simhon | 606/49 |
| 5,088,997 | 2/1992 | Delahuerga et al. | 606/49 |

Primary Examiner—Stephen C. Pellegrino
Assistant Examiner—Ralph A. Lewis

[57] ABSTRACT

The present invention provides a disposable electrosurgical device which is useful in performing laparoscopic surgical procedures. This electrosurgical device has suction and irrigation capabilities in which the application of electrosurgical current, the application of suction, and the transmission of irrigation fluid, to a surgical site, can be conveniently regulated through control mechanisms contained within a surgical handpiece. The mechanisms which regulate the electrosurgical current, the suction, and the irrigation can be conveniently actuated independently with one hand at a single location on the surgical handpiece. A disposable rotatable combined electrosurgical-suction-irrigation probe releasably attaches to the distal end of the surgical handpiece. This probe is an electrically conductive fluid conduit which forms an electrical and fluid connection to the surgical handpiece. It provides an electrical and fluid passageway to an electrocauterizing tip which applies the therapeutic electrosurgical current.

15 Claims, 2 Drawing Sheets

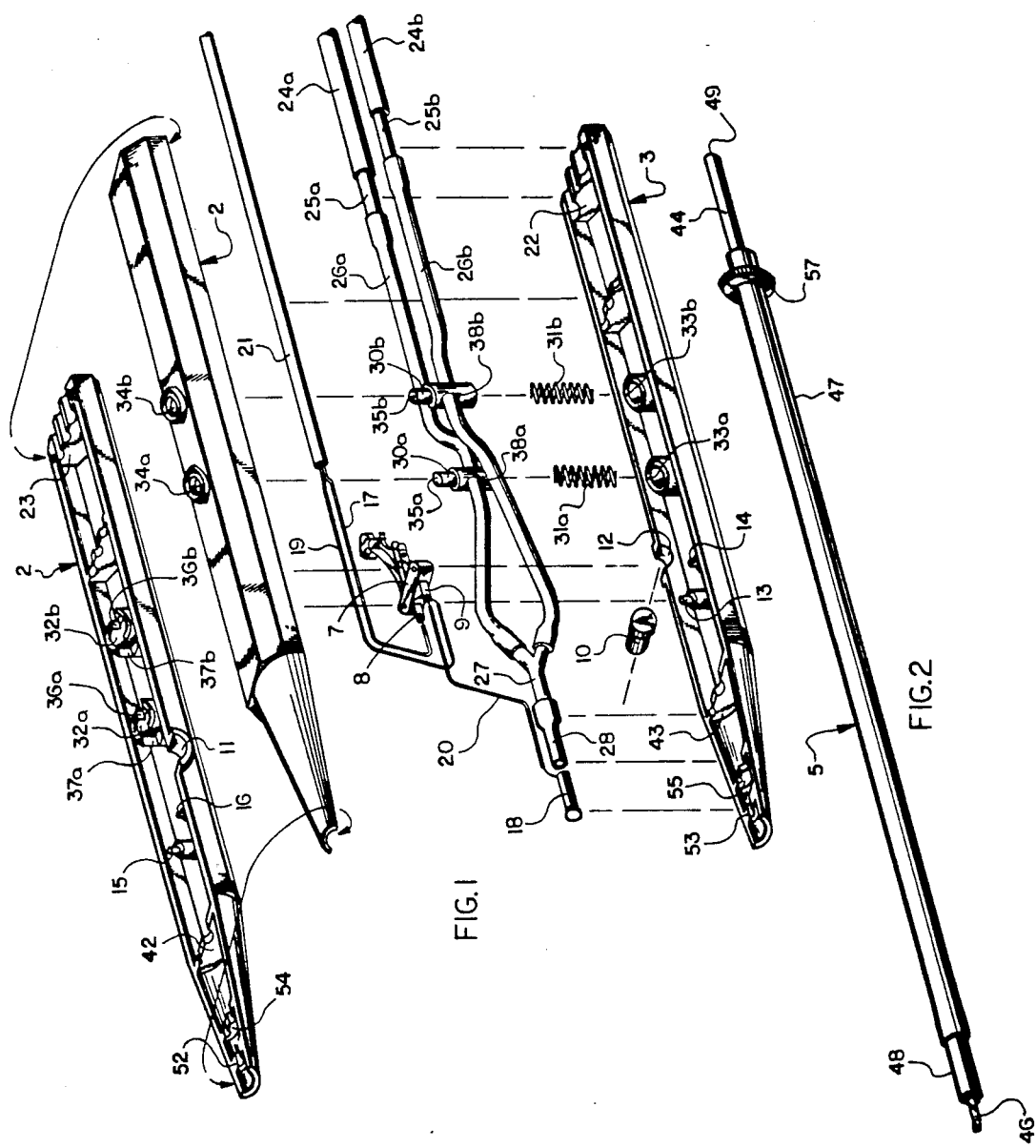

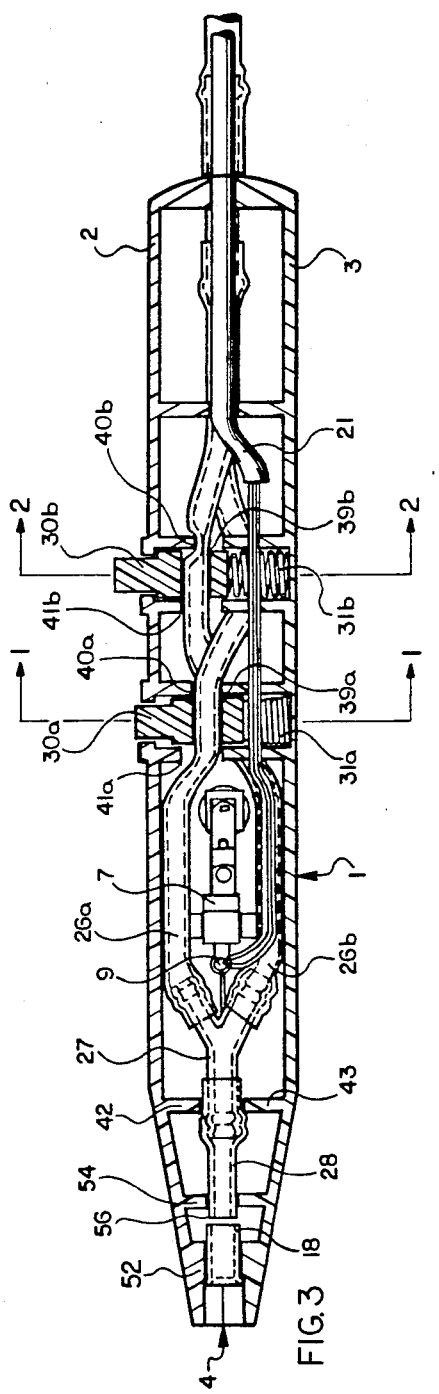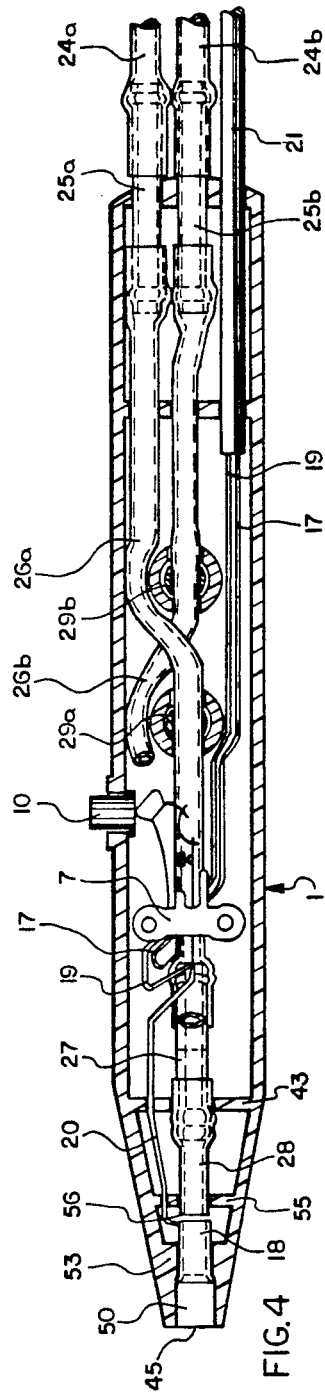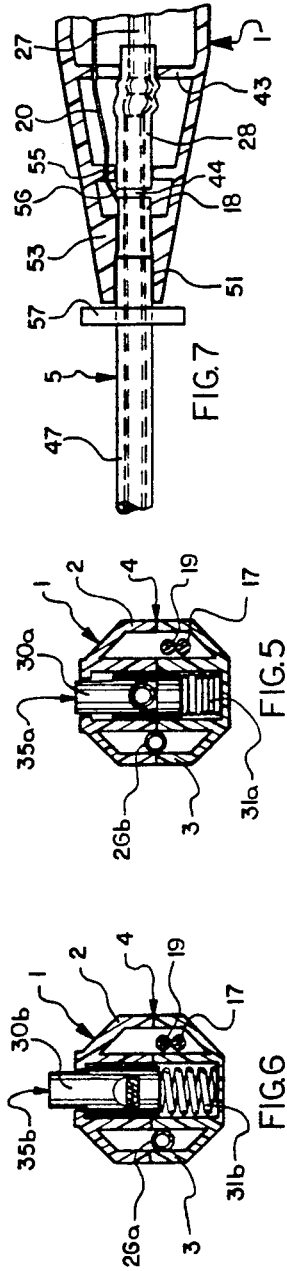

ELECTROSURGICAL DEVICE WITH SUCTION AND IRRIGATION

FIELD OF THE INVENTION

The present invention relates in general to a new and useful disposable electrosurgical device needed to perform laparoscopic surgical procedures and in particular to an electrosurgical device with suction and irrigation capabilities in which the application of high frequency electrosurgical current, the application of suction, and the transmission of irrigation fluid, to a surgical site, can be regulated through control mechanisms contained within a surgical handpiece.

BACKGROUND OF THE INVENTION

Electrosurgery has been performed since the end of the nineteenth century and involves the use of high frequency current conducted to a electrocauterizing tip of an active electrode which in turn generates the heat necessary to cut and coagulate contacted tissue. Because of the development over the years of a multitude of new surgical procedures, many different electrosurgical devices have been developed with a wide variety of unique features.

Recently, there has been, and continues to be, advancement in the development of laparoscopic surgical techniques. These newly developing procedures, using remote video technology, enable the surgeon to perform an operation through a limited number of small incisions in an inflated abdomen eliminating the need for a much larger and more traumatizing abdominal incision. This has created a need for a new multifunctional electrosurgical for device which, until now, there has been no need. Detailed observations of these new surgical techniques have been made in order to determine the design features a device used in these types of operations must have. The results of this work are detailed in the objects of the invention.

DESCRIPTION OF RELATED ART

Hand operated electrosurgical devices with dual switch actuation and plug-in electrosurgical probes with cauterizing tips for cutting tissue and coagulating small bleeders are well known in the art. Many of these devices have no fluid transmission capabilities and have no direct relationship to the present invention. Several of these devices do have some form of fluid transmission capability.

Hyams U.S. Pat. No. 2,102,270 discloses an electrosurgical device for female sterilization procedures having an auxiliary tube surrounding the electric blade for the introduction of a liquid for radiologically monitoring the operation.

Bierman U.S. Pat. No. 2,275,167 discloses an electrosurgical device for removal of tissue by electric current and having means for applying vacuum for drawing in and holding tissue being cut.

August U.S. Pat. No. 2,808,833 discloses an electrosurgical device with a tube for supplying an inert gas to blanket the surgical site.

Seiger U.S. Pat. No. 2,888,928 discloses electrosurgical devices with a tube for withdrawing blood and smoke from the surgical site by vacuum.

Morrison U.S. Pat. No. 3,828,780 discloses an electrosurgical device with a tube for withdrawing blood and smoke from the surgical site by vacuum and having a side vent opening.

Roberts U.S. Pat. No. 3,906,955 discloses an electrosurgical device with a tube for withdrawing blood and smoke from the surgical site by vacuum and constructed for easy replacement of the blade.

Durden U.S. Pat. No. 3,974,833 discloses an electrosurgical device with a tube for withdrawing blood and smoke from the surgical site by vacuum and having a side vent opening arrangement for selective opening and closing to control application of the vacuum.

Walker U.S. Pat. No. 4,562,838 discloses an electrosurgical device with a tube for supplying fluid to the surgical site for removing blood and smoke and having a light transmitting cable for illuminating the surgical site.

Johnson U.S. Pat. No. 4,719,914 discloses an electrosurgical device for withdrawing smoke from surgical areas being cut and cauterized by means of vacuum.

Borsanyi U.S. Pat. No. 4,811,733 discloses an electrosurgical device with a special curved-tip probe for knee surgery.

This prior art exemplifies past invention having certain superficial similarities to the present invention. They all provide means for performing electrosurgery and have some form of fluid transmission capability. However, the capability of these instruments is limited in comparison and is specifically designed for other unrelated surgical procedures.

Electrosurgical devices with suction and irrigation capabilities which are being used in related laparoscopic procedures are fabricated from metal components making them expensive, non-disposable, and electrically uninsulated. The design of these instruments is similar. It provides for a surgical handpiece with only a single valve for irrigation. There is no control valve for suction. An attached stopcock valve must be added to its proximal end for suction control. There is no switch to activate electrosurgical function on the handpiece. A remote foot petal control switch is required. A non-rotatable electrosurgical probe, containing the electrocauterizing tip, is permanently attached to the handpiece.

This type of design creates many problems for the surgeon. An uninsulated metal handpiece can occasionally conduct the high frequency current through thin portions of the surgeon's glove. This can cause unintentional and potentially dangerous trauma to the patient as well as damage to the surgeon's hands. A remote foot-actuated control switch can impede precise activation of the electrosurgical current and requires a sustained uneven weight distribution on the surgeon's feet causing unnecessary fatigue. When attempting to activate the attached stopcock, providing suction control, a major relocation of both hands is required. This is cumbersome, time consuming, and often distracts the surgeon's attention away from the video monitor causing a temporary diminution of perspective as it relates to instrument orientation inside the patient. Different cauterizing tip configurations are required when performing laparoscopic surgical procedures. A surgical handpiece having a permanently attached cauterizing tip forces the surgeon to go through the unnecessary process of unhooking the electrical and fluid inputs independently and connecting them to a new handpiece. These independently protruding input connections are very cumbersome and can also obstruct handpiece manipulation. In addition, a cauterizing tip which is non-rotatable in relation to the surgical handpiece creates a situation where the surgeon must rotate his hand into awkward positions.

The inadequacies of an instrument design of this type are numerous. Their use in surgery causes delays, increases the risk of contamination, and in general, heightens the potential for unnecessary trauma to the patient. Clearly, there is a dramatic need for a unique multifunctional electrosurgical device specifically designed to alleviate the problems outlined above.

OBJECTS OF THE INVENTION

It is the principal object of the invention to provide an inexpensive disposable hand-held electrosurgical device with suction and irrigation in which the application of high frequency electrosurgical current, the application of suction, and the transmission of irrigation fluid, to a surgical site, can be conveniently regulated through control mechanisms contained within a surgical handpiece.

Another object of the invention is to provide an electrosurgical device with suction and irrigation capabilities having two components, a surgical handpiece and an extended axially rotatable surgical probe, which releasably connect together, quickly forming the fluid and electrical connections in one convenient step.

A further object of the invention is to provide an electrosurgical device with suction and irrigation capabilities having the control mechanisms for the electrosurgical current, the suction, and the irrigation capable of being conveniently activated simultaneously or independently with a single hand at a stationary location on the surgical handpiece.

A still further object of the invention is to provide an electrosurgical device with suction and irrigation capabilities in which the fluid and electrical connections are located at a remote location away from the surgical handpiece and the sterile operating field.

SUMMARY OF THE INVENTION

The present invention provides for an electrosurgical device with suction and irrigation capabilities having a unique fluid transmission system which is designed to incorporate the necessary features mentioned in the objects of the invention. This electrosurgical device needs two independent components to operate—the surgical handpiece and a surgical probe. The elongated hand-held surgical handpiece provides means of controlled transmission of electrosurgical current, suction, and irrigation from remote sources to its distal end. This handpiece contains a hand-activated electrical switch which controls the transmission of the electrosurgical current. It also contains two hand-operated control valves which are specially designed conduit collapsing mechanisms regulating fluid transmission through two extended fluid conduits acting as the carriers for the suction and irrigation.

This integrated design minimizes the number and the expense of components used to construct the two valve mechanisms. It incorporates the valve chambers into the two molded plastic shells which form the elongated handle for the surgical handpiece. Inside each of these chambers is a compression spring which acts against a molded plastic valve piston through which a flexible and elastically deformable section of one of the extended fluid conduits pass. This spring applies a compression force against the external walls of this flexible and elastically deformable conduit section, collapsing it, and shutting off fluid transmission. The valve piston protrudes from the handpiece providing an exposed relief button. When actuated, this button relieves the compression force normally being exerted on the conduit, thus, allowing fluid transmission. The rate of this fluid transmission can be regulated by a graduated actuation of a relief button.

The surgical handpiece is designed to allow a single hand, at a stationary location on the surgical handpiece, to separately or simultaneously activate the electrosurgical current with the index finger and the suction or irrigation control mechanisms with the thumb. This is partly accomplished by making the actuation direction of the conduit compression mechanisms perpendicular to the actuation direction of the electrical switch mechanism.

After passing through the conduit compression mechanisms, the suction and irrigation conduits join together into a common conduit which is located in the distal end of the surgical handpiece. Also located in the distal end of the surgical handpiece, is the conductive socket to which the electrosurgical current is transmitted when the electrosurgical switch is activated. A surgical probe, which releasably attaches to the surgical handpiece, forms a releasable electrical connection to this conductive socket and a releasable fluid connection to the common conduit. This surgical probe is essentially a rigid, elongated, insulated conductive conduit which provides a combined fluid and electrical passageway from the surgical handpiece to an attached electrocauterizing tip. This design enables different types of surgical probes, containing differing cauterizing tip configurations, to be conveniently interchanged during surgery without a change in the surgical handpiece. In addition, this design permits complete axial rotation of the surgical probe in relation to the surgical handpiece.

BRIEF DESCRIPTION OF THE DRAWINGS

FIG. 1 is a perspective-exploded view of the bottom of a right hand surgical handpiece illustrating detail of the molded shells which form the handle and the assembly of various component parts;

FIG. 2 is a perspective view of a surgical probe;

FIG. 3 is a longitudinal cross-sectional bottom view of a right hand surgical handpiece bisecting the molded elongated handle and the centrally located fluid components, exposing a preferred view of the suction and irrigation conduit compression mechanisms;

FIG. 4 is a longitudinal cross-sectional side view of a right hand surgical handpiece bisecting the molded elongated handle and the centrally located fluid components, exposing a preferred view of the electrical switching mechanism;

FIG. 5 is a cross-sectional view of the surgical handpiece taken along lines 1—1 of FIG. 1, showing the conduit compression mechanism in a fully actuated position allowing fluid communication;

FIG. 6 is a cross-sectional view of the surgical handpiece taken along lines 2—2 of FIG. 1, showing the conduit compression mechanism in its unactuated position preventing fluid communication;

FIG. 7 is a partial longitudinal cross-sectional view of the distal end of the surgical handpiece and a partial longitudinal cross-sectional view of the surgical probe with its back end fully inserted in to the distal end of the surgical handpiece;

DESCRIPTION OF THE PREFERRED EMBODIMENTS

FIGS. 1-7 illustrates a particular embodiment of a preferred electrosurgical device with extended fluid conduits for providing a controlled application of suction and irrigation to a surgical site in accordance with the present invention.

This preferred electrosurgical device, or what could be defined as a combined electrosurgical-suction-irrigation device, has two independent components—the surgical handpiece (see FIG. 1), and the surgical probe 5 (see FIG. 2), which join together to form a complete working electrosurgical device.

The surgical handpiece has an elongated handle 1 which is constructed from two elongated handle halves or shells 2 and 3. These shells 2 and 3 are preferably molded from an electrically nonconductive material which is made from a thermoplastic resin. During assembly, these shells 2 and 3 are brought together along a joining line 4 where they are fused together. The various components, contained within, or protruding from, the elongated handle 1 are held in position by structural support ribs or protrusions molded into shells 2 and 3. There is a distinct distal end and a distinct proximal end to the surgical handpiece. The extended electrical conductors and extended fluid conduits make a proximally oriented entry into the elongated handle 1. The probe 5, which contains the electrically conductive fluid conduit, forms a distally oriented connection to the elongated handle 1. Components contained within the surgical handpiece are defined as having a distal end, which is generally oriented distally within the handpiece, and a proximal end, which is generally oriented proximally within the surgical handpiece.

Contained within the surgical handpiece is an electrical system which transmits electrosurgical current from a remote electrical source to the probe 5 which forms a releasable connection to the distal end of the elongated handle 1. This preferred electrical system provides means for controlling the transmission of this electrosurgical current. This system consists of an electrical switching system and a common electrical conductor. The electrical switching system has an electrical contact switch 7 and an active electrical conductor. The electrical contact switch 7 is a snap action, single pole, single throw, normally open electrical switching device. It has means of making and breaking an electrical connection between two electrical contacts. When the electrical contact switch 7 is activated, there is formed an electrical connection between the active contact, which forms an electrical connection to the active terminal 8, and the common contact, which forms an electrical connection to the switching terminal 9. When the electrical contact switch 7 is unactivated, the two contacts are held apart so that electrosurgical current is not conducted across the space between these contacts. The electrical contact switch 7 is activated by a switch activation button 10 which protrudes through an opening in the elongated handle 1. This opening is formed when two notches 11 and 12, molded in the shells 2 and 3, are brought together during assembly of the surgical handpiece. The electrical contact switch 7 is held in position within the elongated handle 1 by the structural support protrusions 13, 14, 15, and 16. The active electrical conductor is an extended electrical conductor 17 with an adapted end which forms a releasable electrical connection to a remote electrical source. This extended electrical conductor 17 extends away from the remote electrical source, enters into the proximal end of the elongated handle 1, and forms an electrical connection with the active terminal 8 on the electrical contact switch 7.

The common electrical conductor consists of a conductive socket 18 and two electrical conductors 19 and 20. Electrical conductor 19 is an extended electrical conductor which has an adapted end which has means of forming a releasable electrical connection to a remote electrical source. This conductor 19 has means of entry into the proximal end of the elongated handle 1 and forms electrical connections with the switching terminal 9 and the electrical conductor 20. Conductor 20 is electrically insulated and extends distally, forming an electrical connection to the conductive socket 18. The two conductors 17 and 19 are electrically insulated and are tightly surrounded by an electrically insulating conduit 21. This forms an electrical power cord which extends from the remote electrical source of the conductors 17 and 19, enters the proximal end of the elongated handle 1 and continues distally for a short distance. The proximal structural support ribs 22 and 23 compress against a segment of this power cord producing a strain relief between the elongated handle 1 and the power cord.

The preferred surgical handpiece has two extended fluid conduits for the communication of fluid. Each of these extended fluid conduits has an associated conduit collapsing mechanism designed to regulate fluid communication. One of these extended fluid conduits has means of forming a fluid connection to a remote fluid source which provides suction. The other has means of forming a fluid connection to a remote fluid source which provides irrigation.

These two extended fluid conduits and their associated conduit collasping mechanisms are substantially identical except for their location within the surgical handpiece. Components of these two extended fluid conduits, and their associated conduit collapsing mechanisms, which are illustrated in the drawings having identical designation numbers with differing postscripts, are substantially identical. When these designation numbers are referred to without their accompanying postscripts, the description pertains jointly to both components.

The fluid connections contained in this electrosurgical device, including any releasable fluid connections, are substantially identical. They are made when a flexible conduit is joined with a rigid conduit. The internal side walls of the flexible conduit circumferentially expand when forced to overlap the external side walls of the rigid conduit to which it is forming the fluid connection. The elastic memory, contained within the segment of overlapping flexible conduit, provides a circumferential contraction force onto the segment of overlapping rigid conduit. This produces a sealed interface between the external and internal side walls of the two conduits forming the fluid connection. The ends of the conduits are unobstructed, leaving an open passageway for the communication of fluid from one segment of the extended fluid conduit to another.

An extended fluid conduit is created by several different conduits linked together by a series of fluid connections forming sealed passageways capable of transmitting fluid. A preferred extended fluid conduit consists of a flexible external conduit 24, a rigid splicer conduit 25, a flexible and deformable conduit 26, a rigid three-way junction conduit 27, and a flexible common conduit 28. The flexible external conduit 24 is constructed from a flexible thermoplastic resin. It has means of forming a releasable fluid connection to a remote fluid source, extends to the proximal end of the elongated handle 1, and forms a fluid connection to the proximal end of the rigid splicer conduit 25. The rigid splicer conduit 25 is constructed from a rigid thermoplastic resin and has means of entry into the proximal end of the elongated handle 1. Conduit 25 acts as a conduit strain relief preventing the components of the extended fluid conduit contained within the elongated handle 1 from being dislocated.

The distal end of the conduit 25 forms a fluid connection to the proximal end of the flexible and elastically deformable conduit 26. This conduit 26 extends distally through, and is acted upon by, a conduit collapsing mechanism. When unactuated, this mechanism applies a collapsing force constricting conduit 26 into a closed-off configuration, preventing fluid communication through the extended fluid conduit. When a conduit collapsing mechanism is actuated, this collapsing force is relieved, permitting the conduit 26 to return to an open configuration, allowing fluid communication through the extended fluid conduit. A graduated actuation of a conduit collapsing mechanism results in a gradual lessening in the degree of constriction of the conduit 26 allowing regualtion of the rate of fluid communication through the extended fluid conduit.

A conduit collapsing mechanism consists of a conduit collapsing chamber 29, a conduit collapsing piston 30, and a compression spring 31. The flexible and elastically deformable conduit 26 extends through this mechanism. The conduit collapsing chamber 29 is formed when the chamber halves 32 and 33 come together during the assembly of the shells 1 and 2. This chamber 29 houses the conduit collapsing piston 30 and the compression spring 31. The spring 31 is compressed into the closed end of the chamber half 33. A large portion of one end of the piston 30 is located in the remainder of the chamber 29. The small remaining portion of the other end of the piston 30 protrudes through an opening 34 in the shell 2 and forms the conduit relief button 35. The piston 30 fits closely to the inner side walls of the chamber 29 allowing it to slide freely from side to side along a linear path inside the chamber 29. This determines the actuation direction of the piston 30 and the compression direction of the spring 31 which are both linear along a line which is perpendicular to both the longitudinal and crossectional joining lines of the shells 1 and 2. The conduit collapsing chamber 29 has two openings in the side support walls which create a longitudinally extended passageway through the chamber 29. This passageway extends perpendicularly to the actuation direction of the piston 30. The openings are created by notches in the side support walls of one or both of the conduit collapsing chamber halves 32 and 33. The notches 36 and 37 extend away from the center line 4 and are positioned at the distal and proximal ends of the chamber half 32. When the shells 2 and 3 come together, during assembly, these notches 36 and 37 form the openings which create the longitudinally extended passageway through the chamber 29. In addition, there is also an opening 38 extending through the piston 30 perpendicular to the actuation direction of the piston 30. All of these openings come into alignment, creating a longitudinally extended passageway through the conduit collapsing mechanism. This alignment occurs when the relief button 35 is pushed inward into a fully actuated position (see FIG. 5). When the conduit collapsing mechanism is in its normal, unactuated position, the openings are in their maximally misaligned position, causing a partial reduction in the size of this passageway (see FIG. 6). Any partial actuation of the relief button 35 results in a misalignment of the openings which lies between an aligned position and a maximally misaligned position. The flexible and elastically deformable conduit 26 extends through this longitudinally extended passageway in the conduit collapsing mechanism. Conduit 26 is preferably constructed from a thermoplastic resin which is flexible and elastically deformable. It must have the ability to retain its integrity when subjected to compression forces designed to collapses its walls into a closed configuration. In addition, conduit 26 has an elastic memory contained within its external walls, which enables it to return to a fully open configuration after the compression force has been relieved. When the openings are fully aligned, the longitudinally extended passageway through the conduit collapsing mechanism is of sufficient size to allow the conduit 26 to extend through the conduit collapsing mechanism with no compression forces acting on it. This allows maximal fluid communication through the extended fluid conduit. When the openings are in their maximally misaligned position, the resulting partially reduced passageway compresses the walls of the conduit 26 completely together into a collapsed configuration, stopping the transmission of fluid through the extended fluid conduit. A misalignment of the openings, between an aligned position and a maximally misaligned position, occurring when the relief button 35 is partially actuated, results in a partially collapsed conduit 26. This enables regulation of the rate of fluid communication through the extended fluid conduit.

A conduit collapsing mechanism is designed to minimize the force required to actuate the relief button 35. The relaxation force of the compression spring 31, pushing on the piston 30, provides the compression force necessary to collapse the conduit 26 into a closed-off configuration. This relaxation force must be overcome in order to actuate the relief button 35. The compression force, which only collapses a small segment of the conduit 26, is applied to the conduit on one side by the proximal edge 39 of the opening 38 in the piston 30, and on the other side by the inside proximal edge 40 of the notch 37. These edges 39 and 40, applying the compression force, extend parallel to the crossectional joining line 4 and are wide enough to allow the space necessary for the collapsing walls of the conduit 26 to expand outward. The other distal edge 41 of the notch 37 extends further away from the joining line 4 than the proximal edge 40 of the notch 36, creating an opening large enough so that no compression force is applied to the conduit 26 at the distal end of a conduit collapsing mechanism. This minimizes the area of the conduit 26 which is being acted upon by the compression forces and results in a minimization of the required relaxation force of the spring 31. After extending through their associated conduit collapsing mechanisms, the two extended fluid conduits have means of linking together to form a common fluid passageway. This common fluid passageway is part of both extended fluid conduits. A three-way rigid junction conduit 27 provides the means for forming this common fluid passageway. It links the two flexible conduits 26a and 26b to the common conduit 28. This junction conduit 27 has three rigid protruding conduits to which each of the flexible conduits 26a, 26b, and 28 make a fluid connection. The junction conduit 27 and the proximal end of the common conduit 28 are held in position by two structural support ribs 42 and 43 which clamp against their overlapping segments.

The common conduit 28, which is part of both extended fluid conduits, has means of forming a releasable fluid connection to an electrically conductive fluid conduit 44. The conductive socket 18, which is a part of the common electrical conductor, also has means of forming a releasable electrical connection with this same electrically conductive fluid conduit 44. The conductive socket 18 and the common conduit 28 are both located at the distal end of the elongated handle 1 where an opening 45 allows the electrically conductive fluid conduit 44 to enter and form these releasable connections.

The electrically conductive fluid conduit 44 is part of the surgical probe 5. This conduit 44 is constructed from a rigid elongated conductive metal preferably made from a corrosion-resistant material. It has means of providing a fluid communication passageway from the extended fluid conduit to a location in close proximity to an electrocauterizing tip 46 at the extreme front end of the surgical probe 5. It also has means of providing an electrical connection from the common electrical conductor to this same electrocauterizing tip 46. This electrocauterizing tip 46 maintains a structural and electrical connection to the extreme front end of the conduit 44. It is made from an electrically conductive, corrosion-resistant material. Preventing conduction of electrical current away from the external walls of the conduit 44 are the non-conductive insulation materials 47 and 48. The materials 47 and 48 tightly surround the external walls of the conduit 44 providing a permanent connection. The surgical probe 5 experiences thermal gradients when the electrocauterizing tip 46 is being used. This occurs most acutely at its front end. The insulation materials 47 and 48 have differing thermal resistance characteristics which enables them to withstand the thermal conditions of the segment of conductive conduit 44 with which they are in contact. These insulation materials 47 and 48 extend from the extreme front end of the conductive conduit 44, along the greater part of its length. There is an uninsulated segment of the rigid electrically conductive fluid conduit 44 extending a short distance away from its back end 49. This uninsulated segment of the conduit 44, along with a short segment of the insulation 47, are inserted into the opening 45 at the distal end of the elongated handle 1. When the surgical probe 5 has been inserted fully, the external walls of a short segment of the insulation 47 fit snugly against, and forms a tight slip fit with, the internal walls of the chamber 50 along an overlapping interface 51 at the distal end of the elongated handle 1 (see FIG. 7). This provides partial structural support for the surgical probe 5 as it makes its releasable attachment to the surgical handpiece. In addition, this overlapping interface 51 provides a passive seal helping to shield the conductive components at the point where the releasable connection is made.

As the surgical probe 5 is inserted, the extreme back end 49 of the rigid conduit 44 slips through the inside of the conductive socket 18. The internal side walls of this conductive socket 18 form a tight slip fit with the external side walls of the front portion of the exposed segment of the electrically conductive conduit 44 providing a releasable electrical connection. In addition this also provides a partial structural support for the surgical probe 5. The conductive socket 18 is compressed between, and partially supported by, the structural support ribs 52 and 53 contained within the shells 2 and 3. As the back end 49 of the rigid extended electrically conductive conduit 44 is inserted through the conductive socket 18 and into its final insertion position, it is forced into the distal end of the flexible common conduit 28 where it forms a releasable fluid connection. The internal side walls of the electrically conductive conduit 44 form a tight slip fit with the external side walls of the front portion of the common conduit 28. The common conduit 28 has just enough structural integrity and elasticity to prevent a proximal collapsing of its external walls as this connection is made.

The distal end of the flexible common conduit 28 is supported by structural support ribs 54 and 55 contained within the shells 2 and 3. A small segment 56 of the common conduit 28 extends distally past these support ribs 54 and 55. As the rigid electrically conductive fluid conduit 44 is inserted, this small segment 56 is forced to expand, increasing its outer diameter. This expansion helps prevent the common conduit 28 from being dislocated proximally as the releasable connection in made. In addition, these support ribs 54 and 55, give added structural support to the surgical probe 5 after forming its releasable connection to the surgical handpiece.

The releasable connections, which are formed at the distal end of the elongated handle 1, are designed to permit full axial rotation of the electrically conductive fluid conduit 44 in relation to the surgical handpiece. The tight slip fit of the surfaces of contact between the surgical probe 5 and the surgical handpiece permits this axial rotation. The surgical probe 5 has a circumferentially enlarged segment 57 extending longitudinally for a short distance near the back end of the insulation 47. It has a longitudinal position which is as far on the back end on the surgical probe 5 as possible without interfering with the insulation overlap interface 51. This enlarged segment 57, which can be knurled or have a non-concentric form, is used to facilitate this axial rotation of the surgical probe 5 in relation to the surgical handpiece.

The actuation direction of the switch activation button 10 is perpendicular to the longitudinal joining line 4 and parallel to the cross-sectional joining line 4. Thus, the actuation direction of the electrical contact switch 7 is perpendicular to the actuation direction of the conduit collapsing mechanisms. There is also a defined longitudinal location of the conduit collapsing mechanisms in relation to the electrical contact switch 7. Thus, a proper hand grip on the handpiece, locating the index finger over the switch activation button 10, and the middle finger and thumb pinching either side of the handpiece, will locate the thumb in close proximity to the relief buttons 35a and 35b. This enables the switch activation button 10 and the relief buttons 35a and 35b to be conveniently actuated separately or simultaneously without an awkward relocation of the hand on the surgical handpiece.

The conduit compression mechanism controlling the communication of suction fluid is located distally in relation to the conduit compression mechanism controlling the communication of irrigation fluid. This configuration, combined with the proper longitudinal location of both conduit collapsing mechanisms, make it slightly more convenient to simultaneously actuate the switch activation button 10 and the distal relief button 35a which controls suction.

There is either a right hand or left hand surgical handpiece which can be produced. This is accomplished by inverting the actuation direction of either the relief buttons 35a and 35b in relation to the switch activation button 10 or the switch activation button 44 in relation to the relief buttons 35a and 35b.

The preferred surgical handpiece has the two extended fluid conduits, the extended common electrical conductor, and the extended active electrical conductor, having a proximally oriented means of entry into the elongated handle 1. The electrically insulating conduit 21, which tightly surrounds the two conductors 17 and 19, is bonded together with the two fluid conduits 24a and 24b for some distance away from the proximal end of the elongated handle 1. This, along with their proximal entry, minimizes the obstructiveness of the electrical conductors and the fluid conduits when the surgical handpiece is in use.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims which are appended.

An alternate surgical handpiece design may not have an electrical switching system. There would be no active electrical conductor and no electrical contact switch 7. The electrosurgical current would be transmitted through the common electrical conduit and controlled from a remote switching system away from the handpiece. Other designs can equip the surgical handpiece with more than one electrical switching system in order to conveniently provide different electrosurgical current intensities to a surgical site.

An electrosurgical device may not be designed to have two independent components. The surgical handpiece and the surgical probe 5 could be permanently attached and the releasable fluid and electrical connections would thus not be releasable.

What is claimed:

1. A combined electrosurgical-suction-irrigation device comprising:
   an elongated handle having a distinct distal end and a distinct proximal end;
   an electrocauterizing tip which forms a connection to the extreme distal end of the elongated handle;
   a switching means providing controlled transmission of electrosurgical current to the electrocauterizing tip, wherein the switching means can be activated by a switch mechanism distally oriented within the elongated handle;
   a first fluid conduit extending through said handle which forms a fluid connection to a remote source of suction and provides a fluid communication passageway to a location in close proximity to the electrocauterizing tip, wherein the first extended fluid conduit is acted upon by a first conduit collapsing mechanism, contained within the elongated handle, which normally applies a collapsing force constricting the first extended fluid conduit into a closed-off configuration preventing fluid communication and when hand actuated relieves said collapsing force returning the first extended fluid conduit to an open configuration allowing fluid communication;
   a second fluid conduit extending through said handle which forms a fluid connection to a remote source of irrigation and provides a fluid communication passageway to a location in close proximity to the electrocauterizing tip, wherein the second extended fluid conduit is acted upon by a second conduit collapsing mechanism, contained within the elongated handle, which normally applies a collapsing force constricting the second extended fluid conduit into a closed-off configuration preventing fluid communication and when hand actuated relieves said collapsing force returning the second extended fluid conduit to an open configuration allowing fluid communication;
   said elongated handle wherein a distally oriented single hand grip, located on the elongated handle, can conveniently position both the index finger over the switch mechanism and the thumb in close proximity to the first conduit collapsing mechanism and the second conduit collapsing mechanism, allowing the controlled transmission of electrosurgical current to the electrosurgical tip, the application suction and irrigation to a location in close proximity to the electrocauterizing tip, to be accomplished separately or simultaneously without a relocation of the distally oriented single hand grip.

2. A combined electrosurgical-suction-irrigation device as set forth in claim 1 wherein the elongated handle is constructed from an electrically nonconductive material.

3. A combined electrosurgical-suction-irrigation device as set forth in claim 1, wherein the connection between the handle and electrocauterizing tip is releasable.

4. A combined electrosurgical-suction-irrigation device as set forth in claim 1 wherein the connection between the handle and electrocauterizing tip is not releasable.

5. A combined electrosurgical-suction-irrigation device as set fourth in claim 1 wherein the connection between the handle and electrocauterizing tip permits full axial rotation of the electrosurgical tip in relation to the elongated handle.

6. A combined electrosurgical-suction-irrigation device comprising:
   an elongated handle having a distinct distal end and a distinct proximal end which is constructed from two handle halves joined along a longitudinal and cross-sectional joining line extending from the distal end to the proximal end;
   an electrocauterizing tip which forms a connection to the extreme distal end of the elongated handle;
   a switching means providing controlled transmission of electrosurgical current to the electrocauterizing tip, wherein the switching means can be activated by a switch mechanism distally oriented within the elongated handle;
   a first fluid conduit extending through said handle which forms a fluid connection to a remote source of suction and provides a fluid communication passageway to a location in close proximity to the electrocauterizing tip, wherein the first extended fluid conduit is acted upon by a first conduit collapsing mechanism, contained within the elongated handle, which normally applies a collapsing force constricting the first extended fluid conduit into a closed-off configuration preventing fluid communication and when hand actuated relieves said collapsing force returning the first extended fluid conduit to an open configuration allowing fluid communication;

a second fluid conduit extending through said handle which forms a fluid connection to a remote source of irrigation and provides a fluid communication passageway to a location in close proximity to the electrocauterizing tip, wherein the second extended fluid conduit is acted upon by a second conduit collapsing mechanism, contained within the elongated handle, which normally applies a collapsing force constricting the second extended fluid conduit into a closed-off configuration preventing fluid communication and when hand actuated relieves said collapsing force returning the second extended fluid conduit to an open configuration allowing fluid communication;

said elongated handle wherein the actuation direction of the switch mechanism is perpendicular to the longitudinal joining line of the two handle halves and parallel to the cross-sectional joining line of the two handle halves;

said elongated handle wherein the actuation direction of the first and second conduit collapsing mechanisms is perpendicular to the longitudinal and cross-sectional joining lines of the two handle halves.

7. A combined electrosurgical-suction-irrigation device as set forth in claim 6 wherein the elongated handle is constructed from an electrically nonconductive material.

8. A combined electrosurgical-suction-irrigation device as set forth in claim 6, wherein the connection between the handle and electrocauterizing tip is releasable.

9. A combined electrosurgical-suction-irrigation device as set forth in claim 6 wherein the connection between the handle and electrocauterizing tip is not releasable.

10. A combined electrosurgical-suction-irrigation device as set forth in claim 6 wherein the connection between the handle and electrocauterizing tip permits full axial rotation of the electrosurgical tip in relation to the elongated handle.

11. A combined electrosurgical-suction-irrigation device comprising:

an elongated handle having a distinct distal end and a distinct proximal end which is constructed from two handle halves joined along a longitudinal and cross-sectional joining line extending from the distal end to the proximal end;

an electrocauterizing tip which forms a connection to the extreme distal end of the elongated handle;

a switching means providing controlled transmission of electrosurgical current to the electrocauterizing tip, wherein the switching means can be activated by a switch mechanism distally oriented within the elongated handle;

a first fluid conduit extending through said handle which forms a fluid connection to a remote source of suction and provides a fluid communication passageway to a location in close proximity to the electrocauterizing tip, wherein the first extended fluid conduit is acted upon by a first conduit collapsing mechanism, contained within the elongated handle, which normally applies a collapsing force constricting the first extended fluid conduit into a closed-off configuration preventing fluid communication and when hand actuated relieves said collapsing force returning the first extended fluid conduit to an open configuration allowing fluid communication;

a second fluid conduit extending through said handle which forms a fluid connection to a remote source of irrigation and provides a fluid communication passageway to a location in close proximity to the electrocauterizing tip, wherein the second extended fluid conduit is acted upon by a second conduit collapsing mechanism, contained within the elongated handle, which normally applies a collapsing force constricting the second extended fluid conduit into a closed-off configuration preventing fluid communication and when hand actuated relieves said collapsing force returning the second extended fluid conduit to an open configuration allowing fluid communication;

said elongated handle wherein the actuation direction of the switch mechanism is perpendicular to the longitudinal and cross-sectional joining lines of the two handle halves;

said elongated handle wherein the actuation direction of the first and second conduit collapsing mechanisms is perpendicular to the longitudinal joining line of the two handle halves and parallel to the cross-sectional joining line of the two handle halves.

12. A combined electrosurgical-suction-irrigation device as set forth in claim 11 wherein the elongated handle is constructed from an electrically nonconductive material.

13. A combined electrosurgical-suction-irrigation device as set forth in claim 11, wherein the connection between the handle and electrocauterizing tip is releasable.

14. A combined electrosurgical-suction-irrigation device as set forth in claim 11 wherein the connection between the handle and electrocauterizing tip is not releasable.

15. A combined electrosurgical-suction-irrigation device as set forth in claim 11 wherein the connection between the handle and electrocauterizing tip permits full axial rotation of the electrosurgical tip in relation to the elongated handle.

* * * * *